US00PP23404P2

(12) United States Plant Patent
Hanes

(10) Patent No.: US PP23,404 P2
(45) Date of Patent: Feb. 19, 2013

(54) ***PELARGONIUM* PLANT NAMED 'PEQZ0002'**

(50) Latin Name: ***Pelargonium* interspecific**
Varietal Denomination: PEQZ0002

(75) Inventor: Mitchell E. Hanes, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 13/317,451

(22) Filed: Oct. 18, 2011

(51) Int. Cl.
*A01H 5/00* (2006.01)

(52) U.S. Cl. ..... Plt./324

(58) Field of Classification Search ..... Plt./324
See application file for complete search history.

*Primary Examiner* — Kent L Bell
(74) *Attorney, Agent, or Firm* — Joshua D. Price

(57) ABSTRACT

A new *Pelargonium* plant named 'PEQZ0002' particularly distinguished by the brilliant red-purple flowers, fairly large inflorescences, relatively long peduncles, medium green foliage without zonation, and moderately tall, rounded plant habit

1 Drawing Sheet

Latin name of the genus and species of the plant claimed: *Pelargonium* interspecific.

Varietal denomination: 'PEQZ0002'.

BACKGROUND OF THE NEW PLANT

The present invention comprises a new (hybrid) *Geranium*, botanically known as *Pelargonium* interspecific, and hereinafter referred to by the variety name 'PEQZ0002'.

'PEQZ0002' is a product of a planned breeding program. The new cultivar has brilliant red-purple flowers, fairly large inflorescences, relatively long peduncles, medium green foliage without zonation, and moderately tall, rounded plant habit.

'PEQZ0002' originated from a hybridization made in January 2007 in a controlled breeding program in Gilroy, Calif. USA. The female parent was the proprietary, unpatented plant, a *Pelargonium* interspecific hybrid, designated '10310-2', with hot pink, semi-double flowers, and relatively light green foliage.

The male parent of 'PEQZ0002' was the proprietary *Pelargonium* interspecific hybrid plant '10299-2', unpatented, with orchid colored, single-type flowers, and relatively light green leaves. The resulting seeds were sown in May 2007.

'PEQZ0002' was selected as one flowering plant within the progeny of the stated cross in September 2007 in a controlled environment in Gilroy, Calif.

The first act of asexual reproduction of 'PEQZ0002' was accomplished when vegetative cuttings were propagated from the initial selection in September 2007 in Gilroy, Calif. USA.

BRIEF SUMMARY OF INVENTION

Horticultural examination of plants grown from cuttings of the plant initiated in September 2007 in Gilroy, Calif., and continuing thereafter, has demonstrated that the combination of characteristics as herein disclosed for 'PEQZ0002' are firmly fixed and are retained through successive generations of asexual reproduction.

'PEQZ0002' has not been observed under all possible environmental conditions. The phenotype may vary significantly with variations in environment such as temperature, light intensity and day length.

Plant Breeder's Rights for this cultivar were applied for in Switzerland on Dec. 16, 2010, #10-2701, in Canada on Dec. 17, 2010, #10-7128, and in the European Union Community Plant Variety Office (CPVO) on Jan. 6, 2011, #2011/0067. 'PEQZ0002' has not been made publicly available more than one year prior to the filing of this application.

The following traits have been repeatedly observed and are determined to be basic characteristics of the new variety. The combination of these characteristics distinguishes this *Pelargonium* as a new and distinct variety.

BRIEF DESCRIPTION OF THE PHOTOGRAPH(S)

The accompanying photographic drawing shows typical flower and foliage characteristics of 'PEQZ0002' with colors being as true as possible with an illustration of this type. The photographic drawing shows a flowering plant and a close-up view of a flower of the new variety.

DETAILED BOTANICAL DESCRIPTION

The plant used for the photographs were about 10-11 weeks old, grown in Gilroy, Calif. USA, in a greenhouse trial. The photograph was taken in the end of March 2011.

The plant descriptions and measurements were taken in Hillscheid, Germany in May 2010 on 11 week old plants that were growing in a greenhouse. Cultivation of these plants had started in mid February 2010 when rooted cuttings were planted into 12 cm pots and grown without pinching at a minimum day temperature of 16° C. until April 1 and cool morning culture for keeping plants compact. After April 1st, temperature was generally higher.

Color Chart used: Royal Horticultural Society Colour Chart (R.H.S.) 2001

TABLE 1

DIFFERENCES BETWEEN THE NEW VARIETY 'PEQZ0002' AND A SIMILAR VARIETY

| | 'PEQZ0002' | 'Cante Laver' (U.S. Plant Pat. No. 18,081) |
|---|---|---|
| Plant height: | Taller | Shorter |
| Flower size: | Larger | Smaller |
| Inflorescence size: | Somewhat larger | Somewhat smaller |
| Flower color: | Deeper/bolder | Not as bold or deep |

Plant:

*Form, growth and habit*.—Vigorous, mounded, well branched with tight, foliage canopy; initially more upright and then becoming more spreading.

*Plant height*.—16.0 cm.

*Plant height* (*inflorescence included*).—26.3 cm.

*Plant width*.—29.3 cm.

*Number of branches*.—8.0-10.0 cm.

*Fragrance*.—Flowers are not fragrant, but the whole plant has, when touched, a slight aroma.

Roots:

*Number of days to initiate roots*.—About 15 days at about 22 degrees C.

*Number of days to produce a rooted cutting*.—About 21-24 days at 22 degrees C.

*Type*.—Fine, fibrous, free branching.

*Color*.—RHS N155B.

Foliage:

*Immature leaf, color of upper surface*.—RHS 137D.

*Immature leaf, color of lower surface*.—Between RHS 143C and RHS 144B.

*Mature leaf, color, upper surface*.—RHS 137C to RHS 137D.

*Mature leaf, color of lower surface*.—Between RHS 143B and RHS 144A.

*Length*.—4.6-5.2 cm.

*Width*.—7.5-8.5 cm.

*Shape*.—Kidney-shape to nearly round, with stronger distinctness of lobes.

*Base shape*.—Cordate, with open to nearly closed gap between the lowest lobes.

*Apex shape*.—Rounded.

*Margin*.—Bi-crenate; slightly wavy.

*Texture*.—Velvety, both surfaces pubescent.

*Leaf zone*.—Usually absent, weak traces may occasionally be visible of about RHS 147A.

*Color of veins, upper surface*.—RHS 137D, indistinct in upper portion.

*Color of veins, lower surface*.—RHS 144C.

*Petiole, color*.—RHS 143B to RHS 144A.

*Petiole, length*.—Between 5.5 and 7.0 cm.

*Diameter of petiole*.—0.2-0.3 cm.

*Texture of petiole*.—Densely covered with short hair, some glandular hair.

Stem:

*Number of branches*.—8-10.

*Color of stem*.—Between RHS 143B and RHS143C.

*Length of stem*.—Approx. 11.0-15.0 cm.

*Diameter*.—0.6-0.8 cm.

*Length of internodes*.—1.0-2.5 cm.

*Texture*.—Densely covered with short glandular hair.

Peduncle:

*Color*.—RHS 143B.

*Length*.—About 16.0-16.3 cm.

*Diameter*.—0.3-0.4 cm.

*Texture*.—Dense with both glandular hair and somewhat longer soft hair.

Pedicel:

*Color*.—RHS 183A or a less deep hue with RHS 177B and base RHS146C.

*Length*.—3.9-4.3 cm.

*Diameter*.—0.1-0.2 cm.

*Texture*.—Short glandular hair.

Inflorescence:

*Type*.—An umbel, semi-spherical or nearly semi-spherical, tight, medium sized.

*Blooming habit*.—Beginning of flowering with 50% of plants with open flowers: About mid-April, on about 9-week-old plants.

*Number of inflorescences per plant*.—4-5.

*Number of flowers and buds per inflorescence*.—20-30.

*Umbel diameter*.—11.5-13.0 cm.

*Umbel depth*.—6.5-7.0 cm.

Bud (just before opening):

*Color*.—Closest to RHS 67B.

*Length*.—1.5-1.8 cm.

*Width*.—0.8-0.9 cm.

*Shape*.—Elliptical.

Corolla:

*Form and shape*.—Appears almost single-type, zygomorphic.

*Flower diameter*.—5.2-5.5 cm.

*Depth of flower*.—Approximately 1.5-2.0 cm.

*Number of petals*.—5-6, with a few petaloids.

Upper petals:

*Color upper surface*.—Upper part RHS N74A; lower part (towards base) about RHS 73D to RHS N155B; with RHS 67A veins, and possibly small dots of RHS N66B.

*Color lower surface*.—RHS 67B to RHS N74B.

*Length*.—2.6-2.7 cm.

*Width*.—2.0-2.4 cm.

Lower petals:

*Color upper surface*.—RHS N74A.

*Color lower surface*.—RHS 64C to RHS N74B.

*Length*.—2.4-2.6 cm.

*Width*.—2.3-2.5 cm.

*Petal shape*.—Spathulate to obovate.

*Apex shape*.—Rounded.

*Margin*.—Entire, a little wavy.

*Petal texture*.—Smooth, glabrous.

*Number of petaloids*.—1-4.

*Color petaloids*.—RHS N74A for the upper surface, RHS 73D to RHS N74B for the lower side.

*Petaloid shape*.—Narrower and smaller than the petals, often oblanceolate, possibly curled or twisted.

*Size of petaloids*.—Approximately 0.8-1.8 cm in length, 0.3-0.8 cm wide.

Calyx:

*Number of sepals*.—5, in a whorl, fused at the base.

*Color of sepals, abaxial surface*.—RHS 143A to RHS143B, base may be slightly brown, near RHS 177B.

*Color, adaxial* (*inner*) *surface*.—RHS 143B to RHS143C.

*Length of sepals*.—1.0-1.2 cm.

*Width of sepals.*—0.5 cm (largest sepal), 0.3 cm for the other ones.
*Sepal shape*.—Lanceolate.
*Apex shape*.—Acute.
*Margins*.—Entire.
*Texture outer surface*.—Glandular hair and some longer, soft hair.
*Texture inner surface*.—Smooth, glabrous.

Reproductive organs:

*Pistil.*—1.
*Length.*—0.7-0.9 cm.
*Style color*.—RHS N66C.
*Style length.*—0.4-0.5 cm.
*Stigma color*.—RHS 67B.
*Ovary color*.—RHS 138B.
*Number of stamen.*—3-7.
*Length of anthers.*—0.8-1.0 cm.
*Anther color*.—RHS 47C.
*Length filaments.*—0.6-0.8 cm.
*Color of filaments*.—RHS 67B, fading to RHS155A towards base.
*Pollen amount*.—Little to moderate.
*Color of pollen*.—RHS 25A.
*Fertility/seed set*.—Has not been observed on this hybrid.
*Disease/pest resistance*.—Has not been observed on this hybrid.

What is claimed is:

1. A new and distinct variety of *Pelargonium* plant named 'PEQZ0002' substantially as illustrated and described herein.

* * * * *

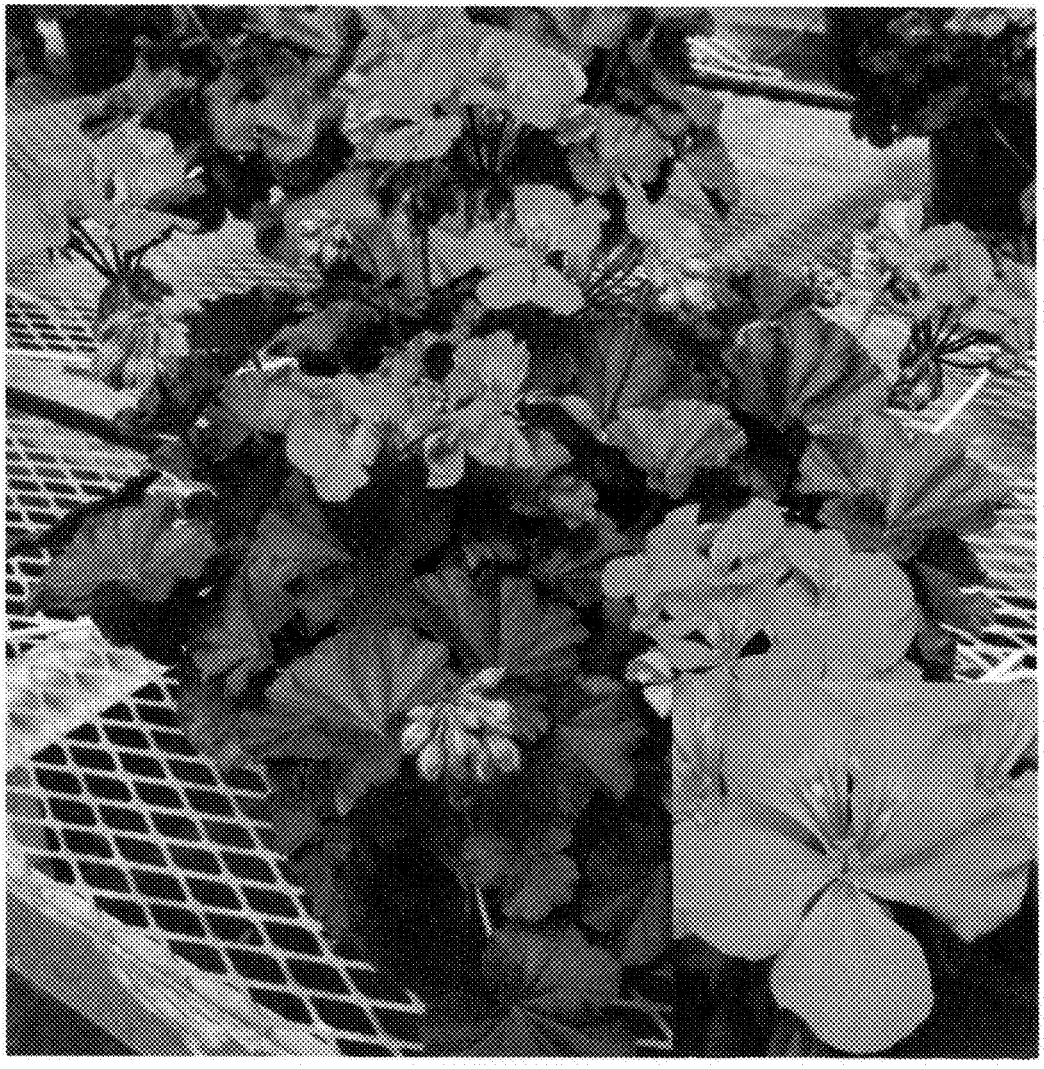

UNITED STATES PATENT AND TRADEMARK OFFICE

CERTIFICATE OF CORRECTION

PATENT NO. : PP23,404 P2
APPLICATION NO. : 13/317451
DATED : February 19, 2013
INVENTOR(S) : Hanes It is certified that error appears in the above-identified patent and that said Letters Patent is hereby corrected as shown below:

Title Page, item (74), Attorney, Agent, or Firm, remove "Joshua D. Price" and insert therefor --Joshua L. Price--

At column 4, line 65, remove "RHS143C" and insert therefor --RHS 143C--

At column 6, line 4, remove "RHS155A" and insert therefor --RHS 155A--

Signed and Sealed this
Ninth Day of April, 2013

Teresa Stanek Rea
*Acting Director of the United States Patent and Trademark Office*